(12) United States Patent
Bayer et al.

(10) Patent No.: US 11,852,356 B2
(45) Date of Patent: Dec. 26, 2023

(54) HEATING APPARATUS

(71) Applicant: ResMed Pty Ltd, Bella Vista (AU)

(72) Inventors: Christian Bayer, Penzberg (DE);
Robert Eibl, Bad Töelz (DE); Johann Sebastian Burz, Germaringen (DE); Achim Biener, Aufkirchen (DE); Bernd Christoph Lang, Graefelfing (DE); Jens Rothfuss, Unterschleissheim (DE); Johannes Nickol, Neukenroth (DE); Andreas Kirchberger, Miesbach (DE)

(73) Assignee: ResMed Pty Ltd, Bella Vista (AU)

( * ) Notice: Subject to any disclaimer, the term of this patent is extended or adjusted under 35 U.S.C. 154(b) by 532 days.

(21) Appl. No.: 16/432,513

(22) Filed: Jun. 5, 2019

(65) Prior Publication Data

US 2019/0390863 A1 Dec. 26, 2019

Related U.S. Application Data

(63) Continuation of application No. 14/384,639, filed as application No. PCT/EP2012/071739 on Nov. 2, 2012, now Pat. No. 10,317,098.

(Continued)

(51) Int. Cl.
*F24F 6/10* (2006.01)
*F22B 1/28* (2006.01)
(Continued)

(52) U.S. Cl.
CPC .............. *F24F 6/10* (2013.01); *A61M 16/109* (2014.02); *A61M 16/16* (2013.01);
(Continued)

(58) Field of Classification Search
None
See application file for complete search history.

(56) References Cited

U.S. PATENT DOCUMENTS 3,672,568 A * 6/1972 Foote ..................... F24H 1/00
236/44 R
3,694,622 A 9/1972 Bentley
(Continued)

FOREIGN PATENT DOCUMENTS

| WO | 2008/148154 | 12/2008 |
| WO | 2010/031126 | 3/2010 |
| WO | 2012/171072 | 12/2012 |

OTHER PUBLICATIONS

Extended European Search Report dated Jul. 30, 2020 in European Application No. 19218469.5, 8 pages.

(Continued)

*Primary Examiner* — Thor S Campbell
(74) *Attorney, Agent, or Firm* — Nixon & Vanderhye P.C.

(57) ABSTRACT

The present technology relates to a tub for a humidifier comprising a container made of a first material, a heating element, and a lining made of a second, preferably biocompatible, material different from the first material, wherein the container comprises a base and a side wall defining a reservoir for a supply of liquid to be evaporated, the heating element is provided on the base of the container, and the lining covers the heating element and a substantial portion of the inner surface of the side wall of the container.

23 Claims, 6 Drawing Sheets

Related U.S. Application Data

(60) Provisional application No. 61/611,137, filed on Mar. 15, 2012.

(51) Int. Cl.

| | | |
|---|---|---|
| *A61M 16/10* | (2006.01) | |
| *A61M 16/16* | (2006.01) | |
| *B29C 45/14* | (2006.01) | |
| *B29K 21/00* | (2006.01) | |
| *B29K 101/12* | (2006.01) | |
| *B29L 31/34* | (2006.01) | |

(52) U.S. Cl.
CPC ..... *A61M 16/161* (2014.02); *B29C 45/14819* (2013.01); *F22B 1/284* (2013.01); *A61M 2205/0216* (2013.01); *A61M 2205/0233* (2013.01); *A61M 2205/0238* (2013.01); *A61M 2205/21* (2013.01); *A61M 2205/3331* (2013.01); *A61M 2205/3368* (2013.01); *A61M 2205/3389* (2013.01); *A61M 2205/3633* (2013.01); *B29K 2021/003* (2013.01); *B29K 2101/12* (2013.01); *B29L 2031/3481* (2013.01)

(56) References Cited

U.S. PATENT DOCUMENTS

| | | | | |
|---|---|---|---|---|
| 3,809,374 | A * | 5/1974 | Schossow | F24H 1/00 |
| | | | | 261/130 |
| 4,222,971 | A * | 9/1980 | Eilert | F24F 6/06 |
| | | | | 261/92 |
| 5,522,523 | A * | 6/1996 | Nogles | F24H 1/183 |
| | | | | 220/567.3 |
| 5,546,926 | A * | 8/1996 | Lake | F24F 6/02 |
| | | | | 126/113 |
| 5,752,498 | A * | 5/1998 | Lake | F24F 6/02 |
| | | | | 126/113 |
| 7,049,558 | B2 | 5/2006 | Baer | |
| 10,317,098 | B2 * | 6/2019 | Bayer | A61M 16/161 |
| 2003/0013253 | A1 | 7/2003 | Lipscombe | |
| 2003/0132535 | A1 * | 7/2003 | Lipscombe | A61M 16/1075 |
| | | | | 261/142 |
| 2004/0182849 | A1 | 9/2004 | Shozo et al. | |
| 2007/0125376 | A1 * | 6/2007 | Reinstadtler | F22B 1/284 |
| | | | | 128/203.26 |
| 2008/0072900 | A1 * | 3/2008 | Kenyon | A61M 16/16 |
| | | | | 128/204.18 |
| 2008/0245365 | A1 * | 10/2008 | Genger | A61M 16/109 |
| | | | | 128/204.14 |
| 2008/0257346 | A1 * | 10/2008 | Lathrop | A61M 16/0066 |
| | | | | 128/204.17 |
| 2009/0000620 | A1 * | 1/2009 | Virr | H05B 6/108 |
| | | | | 128/203.27 |
| 2009/0320840 | A1 | 12/2009 | Klasek et al. | |
| 2010/0132708 | A1 * | 6/2010 | Martin | A61M 16/109 |
| | | | | 128/204.17 |
| 2010/0147299 | A1 * | 6/2010 | Row | H05B 3/48 |
| | | | | 128/203.27 |
| 2011/0017212 | A1 * | 1/2011 | Kenyon | A61M 16/024 |
| | | | | 128/203.26 |
| 2011/0023874 | A1 * | 2/2011 | Bath | A61M 16/109 |
| | | | | 128/202.22 |
| 2011/0155132 | A1 * | 6/2011 | Virr | A61M 16/16 |
| | | | | 128/203.26 |
| 2013/0008440 | A1 * | 1/2013 | Maurer | A61M 16/109 |
| | | | | 128/203.12 |
| 2014/0131904 | A1 * | 5/2014 | Tang | A61M 16/109 |
| | | | | 261/142 |
| 2014/0352694 | A1 * | 12/2014 | Row | A61M 16/1075 |
| | | | | 128/203.14 |
| 2015/0115483 | A1 * | 4/2015 | Miller | A61M 16/16 |
| | | | | 261/128 |
| 2015/0202402 | A1 * | 7/2015 | Kat | A61M 16/0066 |
| | | | | 128/203.27 |
| 2019/0390863 | A1 | 12/2019 | Bayer | |

OTHER PUBLICATIONS

International Search Report for PCT/EP2012/071739, dated Mar. 7, 2013, 4 pages.
Written Opinion of the ISA for PCT/EP2012/071739, dated Mar. 7, 2013, 6 pages.
International Preliminary Report on Patentability for PCT/EP2012/071739, dated Sep. 16, 2014, 7 pages.
First Examination Report dated Apr. 21, 2015 in New Zealand Application No. 629805 (2 pages).
European Examination Report dated Jan. 17, 2017 in EP Application No. 12 791 708.6 (6 pages).
Further Examination Report issued in New Zealand Application No. 734898, dated Apr. 27, 2018, 3 pages.
First Examination Report issued in related New Zealand Application No. 734898, dated Sep. 25, 2017, 2 pages.
Final Office Action dated Feb. 14, 2023 in related U.S. Appl. No. 15/973,719, citing U.S. Pat. No. 4,225,542 and U.S. Pat. No. 6,433,317, (14 pages).
Notice of Allowance dated Jun. 7, 2023 in related U.S. Appl. No. 15/973,719, citing U.S. Pat. No. 4,284,878 (Bartels) and U.S. Pat. No. 4,225,542 (Wall) (9 pages).

\* cited by examiner

HEATING APPARATUS

CROSS-REFERENCE TO RELATED APPLICATIONS

This application is a continuation application of U.S. application Ser. No. 14/384,639, filed Sep. 11, 2014, now U.S. Pat. No. 10,317,098, which claims benefit to PCT Application No. PCT/EP2012/071739, filed on Nov. 2, 2012; which claims benefit of Provisional Application No. 61/611,137, filed Mar. 15, 2012, the entire contents of which are hereby incorporated herein by reference.

The present application generally relates to tubs for humidifiers and to methods of manufacturing tubs for humidifiers.

Humidifiers are generally used for a wide range of applications. An important application for a humidifier is a respiratory apparatus which commonly uses devices to alter the humidity of the breathable gas in order to reduce drying of the patient's airway and consequent patient discomfort and associated complications. Such humidifiers are either integrated with, or configured to be coupled to, the respiratory apparatus.

Humidifiers typically comprise a water tub having a capacity of several hundred millilitres, a heating element for heating the water in the tub, a control to enable the level of humidification to be varied, a gas inlet to receive gas from the respiratory apparatus, and a gas outlet adapted to be connected to a gas conduit that delivers the humidified, pressurized flow of breathable gas to the patient's mask. The water in the water tub is typically heated via thermal conduction between the heating element and the tub base of the water tub, which is commonly formed of aluminium or stainless steel. On the one hand, good heat flux between the heating element and the water within the water tub is desirable while on the other the electronics of the heating element and the control should be properly insulated from the water within the water tub.

WO 2008/148154 A1, the content of which is incorporated herein in its entirety, describes inmolded heaters for heating fluids within containers which may be used in a respiratory humidification device. WO 2008/148154 A1 in particular discloses a humidifier comprising a tub configured to contain a supply of water and a heater comprising a first polymer foam having an electrically conductive circuit provided upon a surface, wherein the first polymer foam is electrically insulating and the tub is formed of molded resin and the heater is molded at least partially within the resin. The heater is relatively rigidly secured and molded within the humidifier tub.

The present technology provides a tub for a humidifier. The tub comprises a container made of a first material, a heating element, and a lining including a second, preferably biocompatible, material different from the first material. The container comprises a base and a sidewall defining a reservoir for a supply of liquid to be evaporated. The heating element may be provided on the base of the container and the lining covers at least the heating element. The heating element may be provided additionally or alternatively in other parts of the container, such as on or in one or more side walls. The lining may also cover a substantial portion of the inner surface of the sidewall of the container. Thus, the first material may be chosen to be, e.g., sufficiently stable and/or scratch resistant to provide a stable container. The second material, on the other hand, may be chosen such as to provide a preferably elastic lining which is adapted to electrically insulate the supply of water from the heating element and at the same time accommodate any stress caused by thermal expansion of, e.g., the heating element. In this context, the term "elastic" refers to being adaptable in allowing some expansion and contraction of the material to compensate for expansion and contraction of the heating element in response to changes in temperature. Furthermore, the first material may be chosen to be substantially insulating to heat transport in order to reduce the energy used for keeping the supply of liquid at a predetermined temperature, while the second material may be chosen to be a particularly good heat conductor in order to provide for effective heat transport from the heating element to the supply of liquid.

Accordingly, the tub according to the present technology is advantageous over known tubs for humidifiers in that the use of two different materials allows for a tub design which preferably suits various demands. Furthermore, the tub according to the present technology may be easily manufactured which allows for a cost efficient production process.

The lining may be molded, preferably injection-molded, over the heating element and optionally also over a substantial portion of the inner surface of the sidewall of the container. This further eases the manufacturing and allows for perfect sealing avoiding any creep flow of liquid between the first and second materials towards the heating element. However, other ways to provide for a lining are also envisaged. For example, a pre-manufactured lining may be clamped into the inside of the container or may be attached to the heating element and the inner surface of the sidewall of the container by means of adhesive or any other fastening systems.

In certain aspects the lining may be formed of a plurality of materials wherein at least a portion of the lining is formed of the second material to cover the heater element. For example the lining includes a portion of the elastic or flexible second material covering the heater element coupled with a different material, optionally the same as the first material, that covers the remainder of the internal surface of the humidifier tub. Furthermore, the lining may cover the heater element or the heater element and a substantial portion of the inner surface of the container or humidifier tub. For example, the heating element may be covered with a lining made of silicone, preferably biocompatible silicone, whereas a portion of or essentially the entire internal surface of the container may be molded over with another, preferably harder material.

According to another aspect, the lining is formed entirely of the second material and covers substantially the entire inner surface of the sidewall of the container. This further improves the sealing since the transition region between the first and second materials is most prone to leakage.

The second material may comprise silicone, a thermoplastic elastomer (TPE), or other thermally conductive flexible polymers. Even though the thermal conductivity of silicone is rather low, it may be easily injection-molded in a thin layer over the heating element and the inner surface of the sidewall of the container, thus providing excellent electrical insulation between the liquid within the reservoir and the heating element while still allowing for sufficient heat transport from the heating element to the liquid. Furthermore, silicone is biocompatible and sufficiently flexible to accommodate any stress caused by thermal expansion.

If the second material is biocompatible, such as biocompatible silicone, it may also serve as a barrier against any substances in the first material that are not biocompatible such as Bisphenol A. Thus, the use of a biocompatible second material for the lining allows for the use of various materials for the container which, without such lining, could not be used.

It is further preferred that the first material comprises, preferably consists of, one or a combination of polycarbonate, polysulfone, polymethylmethacrylate, and polybutylene terephthalate. While these materials are known to be easily formable and suitable to provide for a stable container, other materials having similar properties may be used as well.

The lining preferably has a thickness between 0.5 mm and 5 mm, more preferred between 1 mm and 3 mm. A thin lining improves the heat transport while a thicker lining is more durable.

Since the heating element is essentially surrounded by or sealed between the first and second materials, basically any known heating element may be used in the context of the present technology. Suitable heating elements are, inter alia, printed foil heaters, silicone heaters, carbon fiber heaters, etched metal heaters, Kapton heating elements and silicone heating panels. Yet, basically any other known heating element may be used as long as it is sufficiently small and provides sufficient energy to heat the supply of liquid to the required temperature. In certain aspects, the heating element may include the heating element described in U.S. provisional application 61/6,286,622 incorporated herein in its entirety.

According to another aspect, the heating element is coated with an insulating material on at least one side, preferably the bottom side, in order to avoid excessive heat transport from the heating element towards the surrounding of the tub, i.e., to reduce energy waste. Suitable materials are, e.g., silicone and/or silicone foam. However, other materials, in particular, other foams, may be used. The heat insulating material may be complemented with or replaced with a material which reflects thermal radiation, in particular infrared radiation. Thus, heat loss towards the surrounding atmosphere is reduced. Alternatively, or in addition, heat loss may be further decreased by providing a hollow space on one side of, preferably below, the heating element. A particularly preferred aspect combines a hollow, preferably vacuum, space below the heating element with a reflector for infrared radiation.

Preferably, the heating element comprises a plug or connector to electrically connect to the heating element. In one aspect a plug or connector may comprise a tongue with electrical contacts. Furthermore, the tub may comprise one of or different combinations of a temperature sensor, a pressure sensor, a humidity sensor, one or more LEDs, a thermal overload protection and/or means for sensing the level of the supply of liquid such as a capacitive sensor for measuring the water level within the container or reservoir.

The container of the tub may be manufactured by any known means. However, it is preferred to mold, preferably, injection-mold, the container. It is preferred that the tub further comprises a support or supporting structure. The supporting structure preferably comprises one or more of a metal sheet or plate, an aluminium sheet or plate, a (high grade) steel sheet or plate, a fibreglass sheet or plate, and/or a printed circuit board. The supporting structure may increase the stability of the tub and may in particular support and/or protect the heating element from any impacts and/or from stress or strain occurring during the molding process. Preferably, the supporting structure is integral with the heating element. For example, the heating element may be laminated to the supporting structure or the printed circuit board, which provides the support structure, and also comprises the heating element.

In certain aspects, the tub further comprises a lid, wherein the lining provides a sealing for the lid. For example, if the lining covers substantially the entire inner surface of the sidewall of the container, the lid may have a protrusion which fits within the sidewall of the container and engages the lining on the inner surface of the sidewall of the container. Alternatively, or in addition, the lining may form a sealing lip at the top of the container in order to provide a sealing for the lid.

The tub may further comprise a flow plate, wherein the lining provides a sealing for the flow plate.

Further aspects may be directed at a humidifier comprising a base station and a tub as described above. The tub preferably can be removably attached to the base station. It is further preferred that the base station comprises control electronics which can be removably electrically connected to the heating element of the tub.

Further aspects relate to a method of manufacturing a tub for a humidifier, preferably a tub as described above. According to the inventive method, a tool for molding, preferably injection-molding, a container is provided. A heating element is then positioned inside or within said tool and a container is molded, preferably injection-molded, around said heating element. The container is made of a first material and comprises a base and a sidewall defining a reservoir for a supply of liquid to be evaporated, wherein the heating element is arranged on the base and/or sidewalls of the container. Optionally, a supporting structure and/or a plug or connector is provided. Finally, a second, preferably biocompatible, material different from the first material is molded, preferably injection-molded, over at least the heating element and optionally a substantial portion of the inner surface of the sidewall of the container to provide a lining. In case a supporting structure and/or a plug or connector is provided, the second material is also molded over the supporting structure and/or the plug or connector, preferably in such a way as to protect the plug and/or connector from water without affecting or blocking the electrical connections to the base station.

All advantageous and/or preferred features described above with respect to the tub may also be employed for the inventive method. In particular, the materials and dimensions mentioned above with respect to the tub are also preferred for the inventive method.

Preferably, the heating element is preheated to a predetermined temperature before the step of molding the first material. Preferably, the predetermined temperature is between 50° Celsius and 200° Celsius, more preferred between 100° Celsius and 150° Celsius. Preferably, the predetermined temperature is similar or even approximately equal to the molding tool. Thus, the manufacturing process can be more precisely controlled and repeatability can be improved. For example, if the heating element is much colder than the molding tool (e.g. due to its storage) molding may be negatively affected. All the more so if the temperature of the heating element varies from time to time. Keeping the heating element always at the same controlled and predetermined temperature by preheating prevents such variations and possible detrimental effects.

Further details of the tub are described in Australian Provisional Application No. 2011902350, filed Jun. 16, 2011, U.S. Provisional Application No. 61/628,622, filed Nov. 3, 2011 and PCT/AU2012/000693 file 15 Jun. 2012, which are incorporated by reference in its entirety. In particular, PCT/AU2012/000693 describes a heating apparatus including a heating element which converts electrical power to heat energy, a heatable element having a first surface and a second surface, and a dielectric laminate layer between the heating element and the first surface of the heatable element, wherein the dielectric laminate layer is thermally conductive to transfer heat energy from the heating element to the heatable element and wherein the second surface of the heatable element is configured to heat a liquid in a container. For example the heating apparatus may include a lamination of (i) a thermally conductive material, e.g., a hot plate, a metal plate, a thermally conductive substrate layer, (ii) a thermally conductive dielectric laminate layer, (iii) a heating element and (iv) a protective layer. The dielectric laminate layer provides electrical insulation between the heating element and hot plate to, for example, avoid electrical short circuits between the current flowing in the heating element and the hot plate. The heating element may be printed on or otherwise applied to the laminate layer by conventional printing techniques used in Printed Circuit Board (PCB) manufacture and assembly. Alternatively, the heating element may be applied as a sheet to the laminate layer and portions of the sheet etched away to form the tracks of the heating element. The heating element may be a narrow strip of conductive material, e.g., copper foil, arranged in a serpentine pattern.

Further details regarding the thermally conductive laminate layer are described in paragraphs [0059] to [0062], the heating element in paragraphs [0063] to [0065], the protective layer in paragraphs [0066] to [0069], the electrical leads in paragraph [0070] and the contact pads in paragraphs [0071] and [0072], all of which are incorporated by reference.

Preferred arrangements of a tub according to the present technology are further elucidated with reference to the following Figures.

Figure 1:
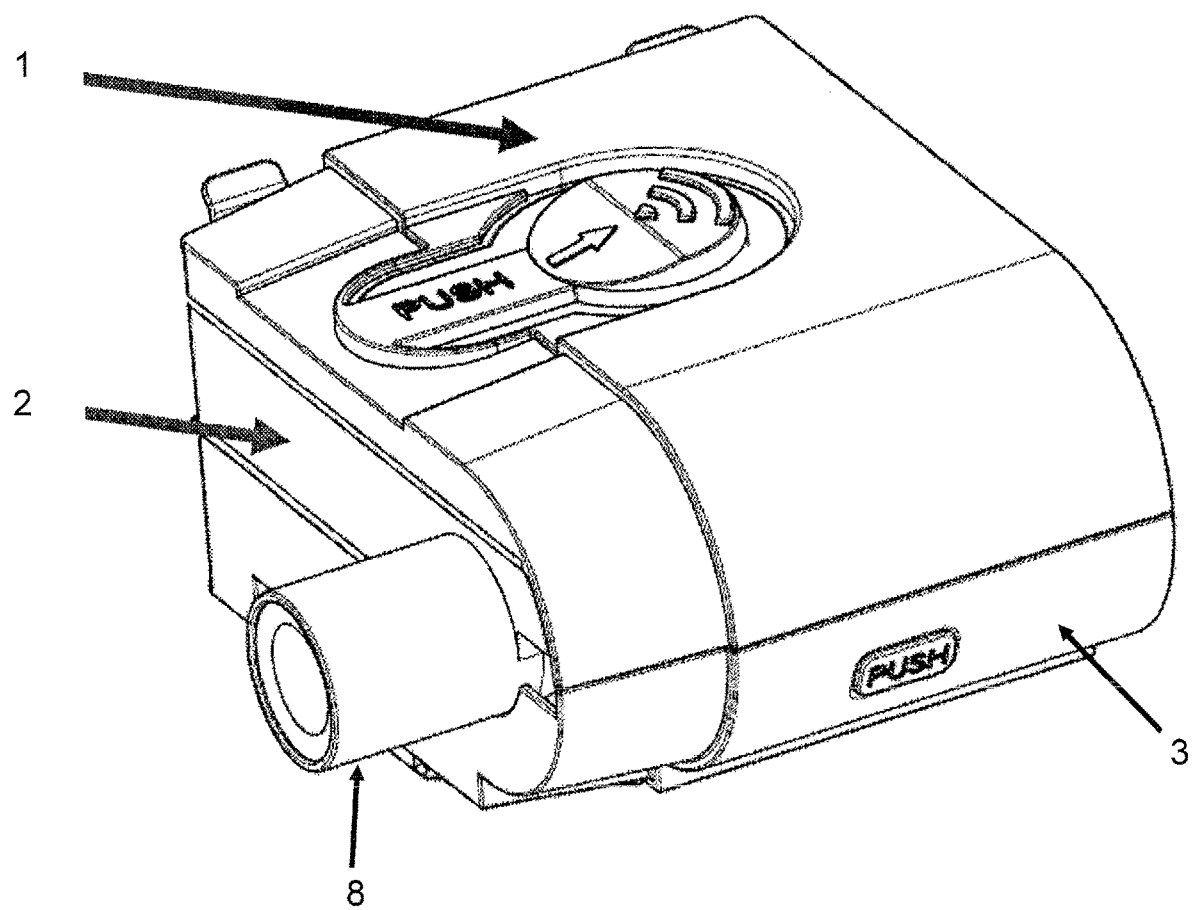
FIGS. 1 to 3 show perspective views of a tub according to an example of the present technology comprising a tub base, a tub center and a tub cover.
Figure 5:
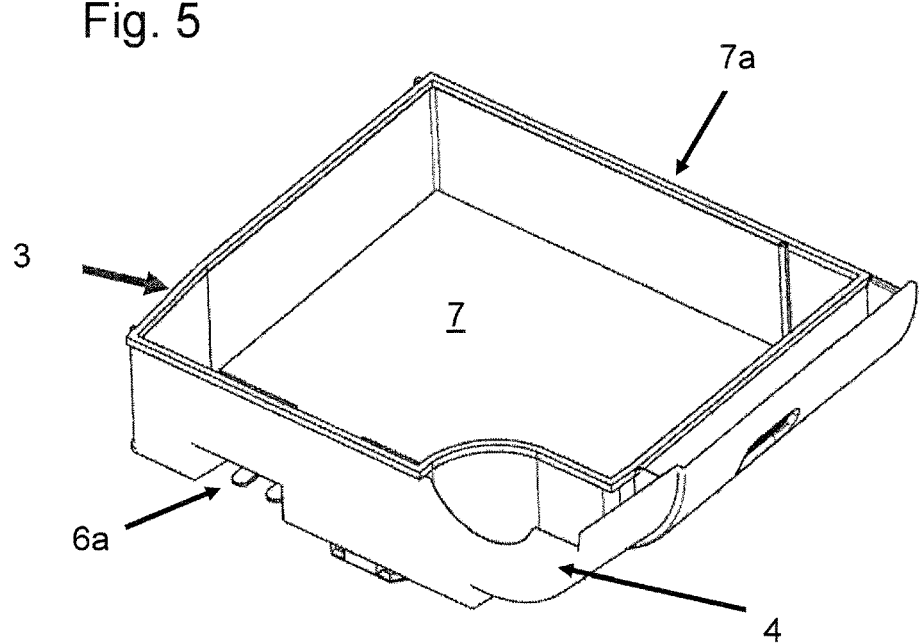
FIG. 5 shows a perspective view of the tub base shown in FIGS. 1 to 4.

FIG. 1 shows a perspective view of a tub module for a humidifier comprising a tub cover or lid 1, a central portion 2 with a humidifier outlet 9 and a humidifier inlet 8, and a tub or tub base 3, which is shown in more detail in the perspective view of FIG. 5. The humidifier outlet 9 may be, e.g., a conical hose nipple such as a 22 mm standard connector according to ISO 5356-1. The humidifier inlet 8 preferably comprises an adapter having a sealing lip 10 (see FIG. 3).

Figure 4:
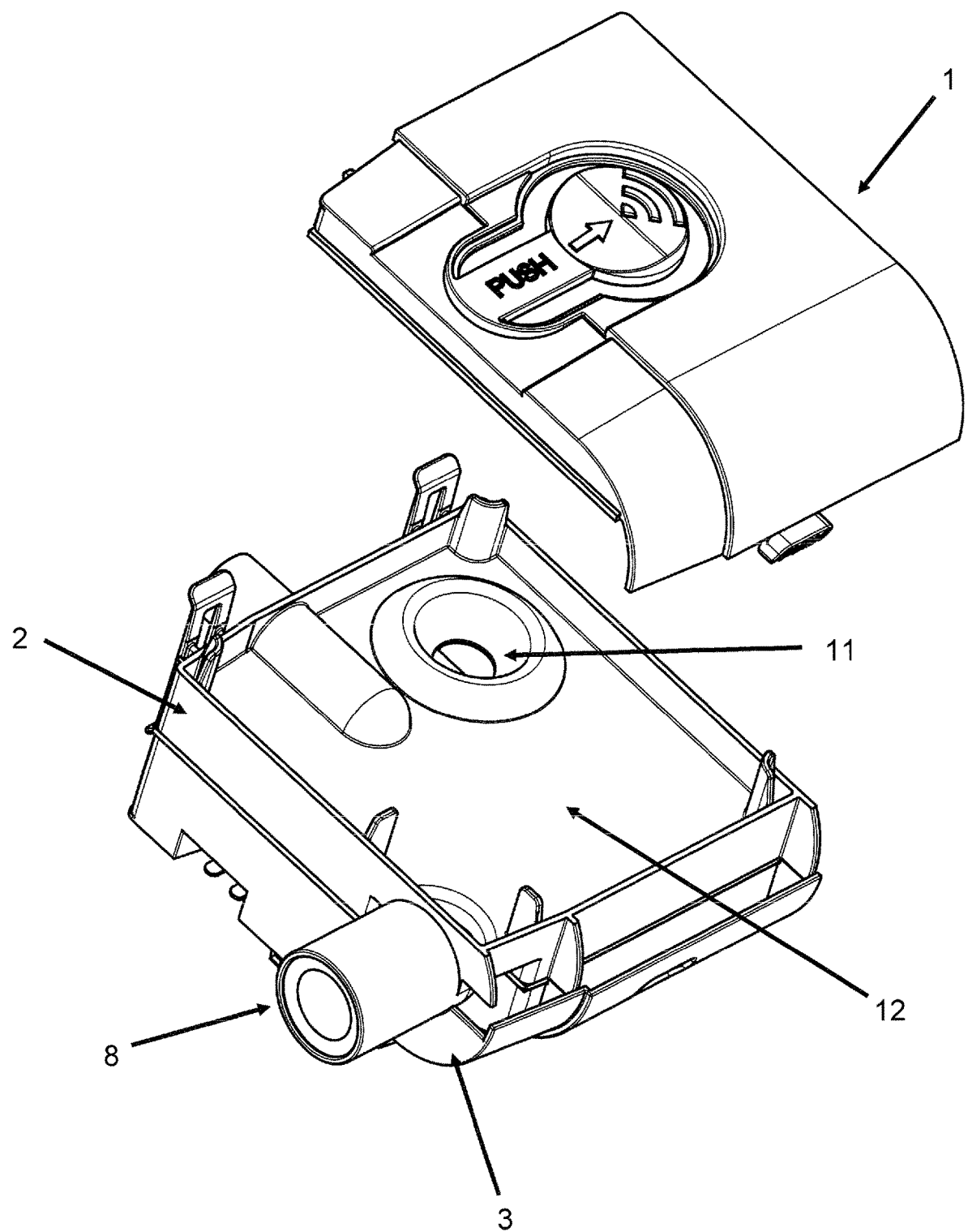
FIG. 4 shows a partially exploded view of the tub of FIG. 1.

Preferably, the central portion 2 comprises a spillback protection. Spillback protection may, e.g., be achieved by an intermediate plate or panel 12 (see FIG. 4) comprising a through hole 11 which is adapted to let air pass from the device via the humidifier inlet 8 to the water reservoir or container(not shown). The air is humidified within said water reservoir before being forwarded to the patient via humidifier outlet 9. If the entire tub module (or the humidifier comprising said tub module) is being tilted, water within the water reservoir may not flow back into the device because the intermediate plate or panel 12 functions as a barrier. Preferably, the through hole 11 is provided at the side opposite the device/device interface in order to improve spillback protection.

Figure 6:
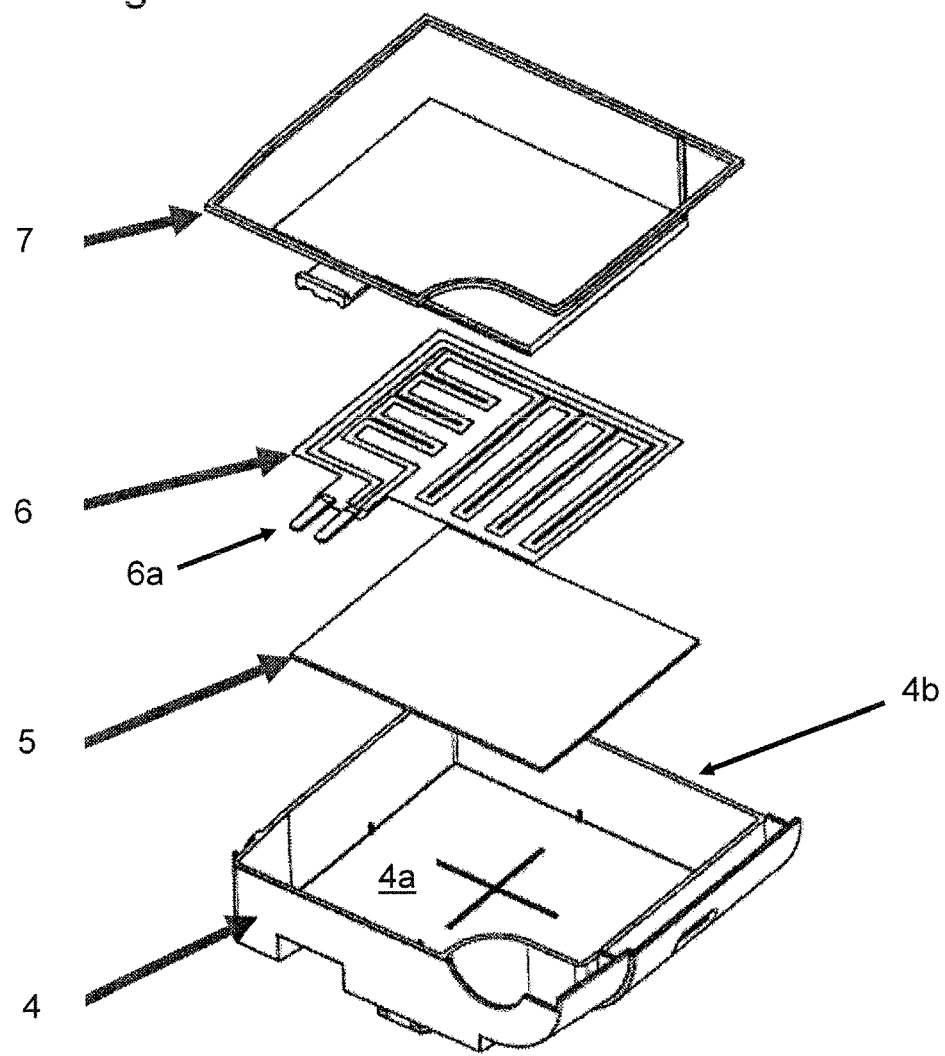
FIG. 6 shows an exploded view of the tub base of FIG. 5.

As may be taken from the exploded view of the tub or tub base 3 shown in FIG. 6, the tub comprises a container 4 made of a first material, a support or supporting structure 5, a heating element 6, and a lining 7 made of a second, different material. The container 4 comprises a base 4a and a sidewall 4b defining a reservoir for supply of liquid to be evaporated. The heating element 6 of this arrangement is provided on the base 4a of the container with the optional supporting structure 5 being arranged therebetween. Alternatively or in addition, a heating element may be provided on another inner surface of the container, e.g. on one or more surfaces of inner sidewall 4b. The lining 7 covers the heating element 6 and optionally essentially the entire inner surface of the sidewall 4b of the container as shown in FIG. 5.

As shown the heating element 6 may comprise a tongue with electrical contacts 6a to electrically connect to the heating element 6. While the supporting structure 5, which is entirely optional, is shown in FIG. 6 as a separate layer or element, it is preferred that supporting structure 5 is integral with the heating element 6. The supporting structure is advantageous in that it may, e.g., protect the heating element during the molding process. In the arrangement shown in FIG. 5, the lining 7 covers essentially the entire inner surface of the sidewall 4b of the container 4 and forms a sealing lip 7a at the top of the container 4. This sealing lip 7a provides a sealing for the tub cover or lid 1 and the central portion 2, respectively.

Figure 2:
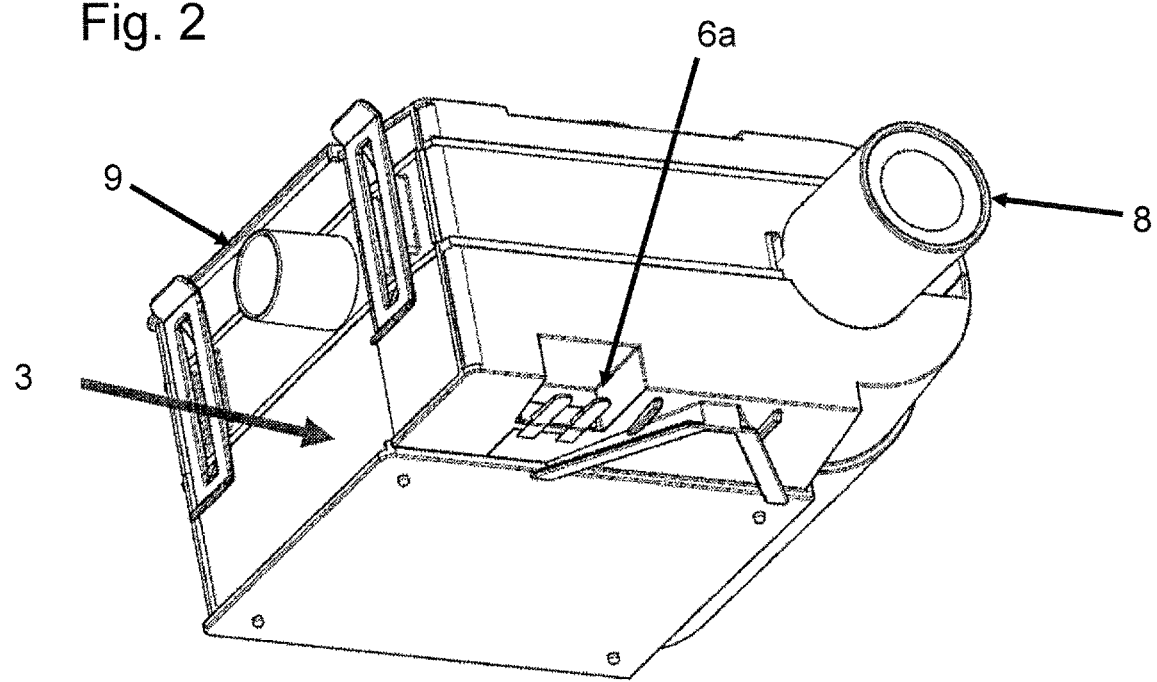
Figure 3:
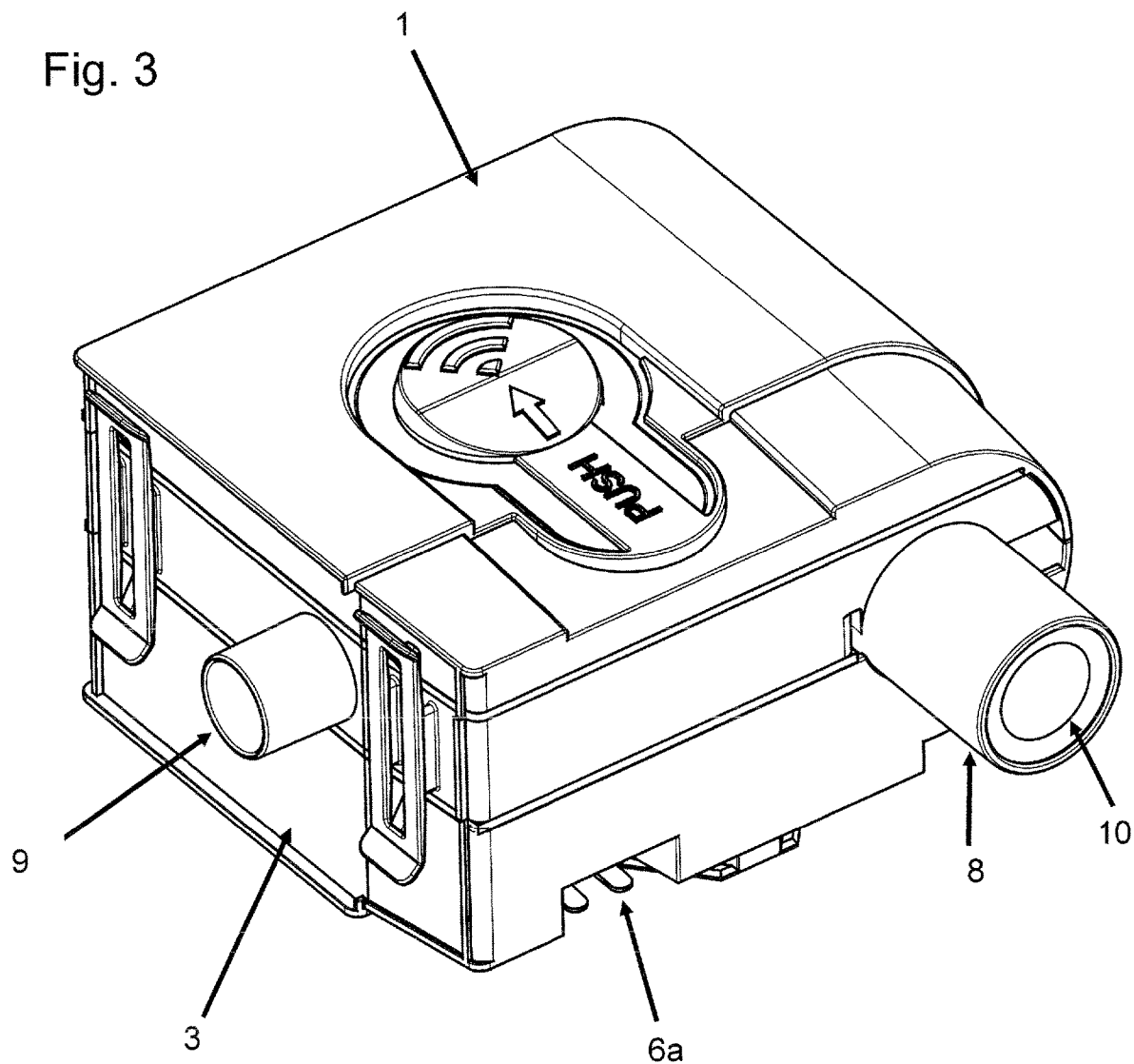

The tub shown in FIGS. 1 to 4 may be removably electrically connected to a base station comprising control electronics via the tongue with electrical contacts 6a of the heating element 6, which protrude from the tub as shown in FIGS. 2 and 3.

While the arrangement shown in FIGS. 1 to 4 comprises rather specific features such as the snap hook interface at the top cover 1 and the device interface and spill back protection at the central portion 2, it is evident that these features are not essential to the present technology and that the claims are not to be construed to be limited to such features. In particular, the entire tub as well as all of its components may have an entirely different geometric shape, e.g., round rather than rectangular or the like. Furthermore, other heating elements than the heating element 6 shown in FIG. 6 may be employed and the lining 7 may not cover the entire inner surface of the sidewall 4b of the container 4, but rather a substantial portion thereof. Moreover, the shape and type of the electrical connections may vary.

Figure 7:
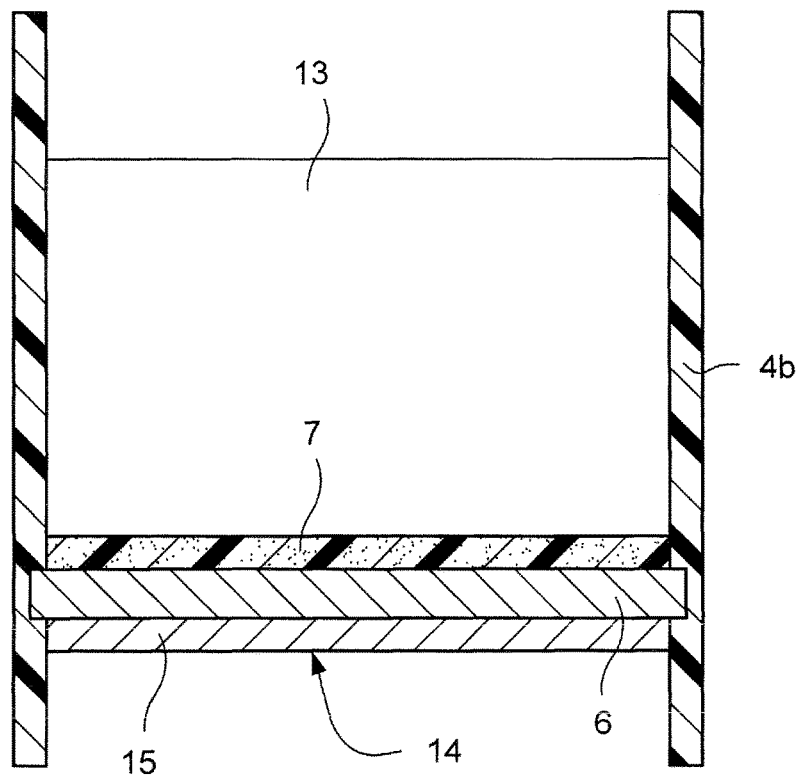
FIG. 7 shows a schematic cross sectional view of a humidifier tub according to an example of the present technology.
Figure 8:
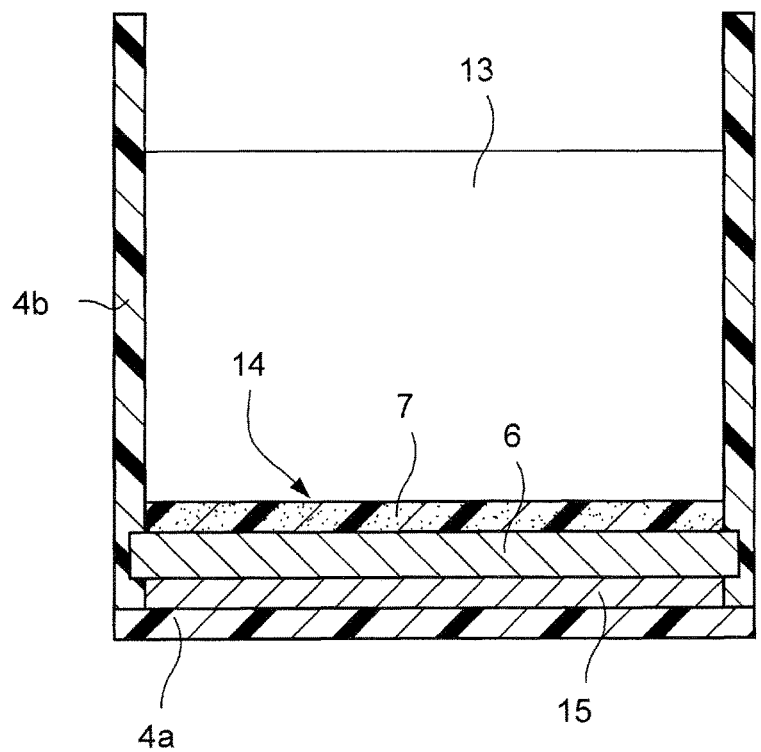
FIG. 8 shows a schematic cross sectional view of a humidifier tub according to an example of the present technology.

FIGS. 7 and 8 show cross sectional views of a humidifier tub according to the present technology. The tub includes a lining 7 provided over the heating element 6. The lining 7 may be overmolded over the heating element 6 to provide a water and/or vapor sealed protection layer across the heating surface. The lining 7 is preferably thermally conductive so as to effectively transfer heat from the hot plate or heating element 6 to the water in the tub. Furthermore the lining 7 is preferably formed of a bio-compatible material and may be formed of silicone, Teflon®, UV cured polymers or other thermally conductive plastic materials, such as CoolPoly™ products. The lining may also provide an easily cleanable surface.

Furthermore, the lining may allow the heating element 6 to be inserted or located directly within the water tub, which may provide enhanced thermal performance.

FIG. 7 shows an example of a humidifier tub with an open base or bottom. As illustrated, the tub includes plastic molded sidewalls 4b and a heating assembly 14 that cooperate to define a water chamber or compartment for water 13. The heating assembly 14 includes an overmolded lining 7, a thermally conductive support structure 15 (e.g., metal hot plate), and a heating element 6 having heating tracks abutting against the support structure 15. As illustrated, the heating assembly is spaced upwardly from the lower ends of the sidewalls 4b. The sidewalls 4b may be overmolded onto the heating apparatus, without a bottom wall or bottom protective layer. Other materials with high thermal insulation may be used for the overmold. Also, an insulator or bottom wall (not shown) may be provided to the tub below the heating element 6.

FIG. 8 shows an example of a humidifier tub with a closed base or bottom 4a. As illustrated, the tub 4 includes plastic molded sidewalls 4b, a plastic molded bottom or base wall 4a, and a heating assembly 14 that cooperate to define a water chamber or compartment for water 13. The heating assembly includes an overmolded lining 7, a thermally conductive support structure 15 (e.g. metal hot plate), and a heating element 6 providing heating tracks. The sidewalls 4b and bottom or base wall 4a may be overmolded onto the heating apparatus.

Figure 9:
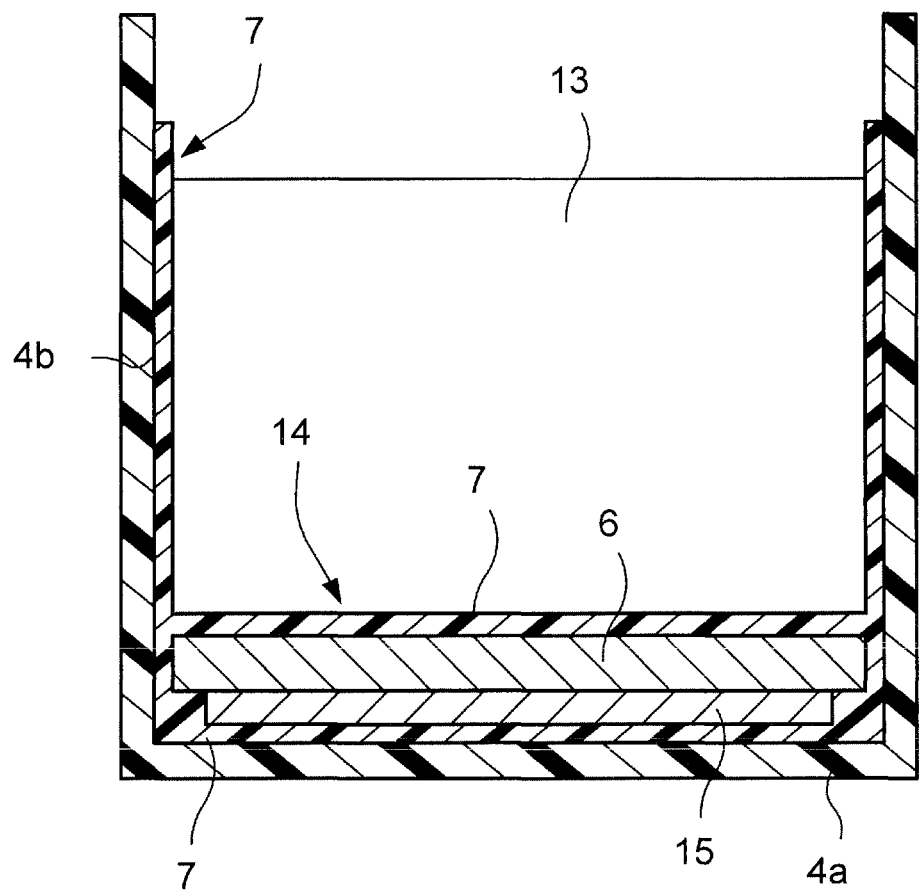
FIG. 9 shows another schematic cross sectional view of a humidifier tub according to an example of the present technology.

FIG. 9 shows another example where the lining 7 is overmolded over the inner surface of the side walls 4b and around the heating assembly 14 at the bottom or base 4a of the tub.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A tub for a humidifier comprising:
a container made of a first material,
a heating element, and
a lining comprising a second material different from the first material, wherein the second material is elastic to, in use, accommodate expansion and contraction of the heating element,
wherein the container comprises a base and a side wall defining a reservoir for a supply of liquid to be evaporated, the heating element being provided only on an inner surface of the base of the container, the lining covering the heating element along the base of the container and also covering an entire inner surface of the side wall of the container, and
wherein the lining is configured to be disposed between the heating element and the supply of liquid, an outer surface of the lining being fixedly adhered directly to 1) the inner surface of the side wall of the container, and 2) the heating element to electrically insulate the supply of liquid from the heating element.

2. The tub of claim 1, wherein a support structure is disposed between the heating element and the base of the container.

3. The tub of claim 1, wherein the lining is molded or injection molded over at least the heating element.

4. The tub of claim 1, wherein the second material comprises silicone, or biocompatible silicone.

5. The tub of claim 1, wherein the heating element is coated with an insulating material.

6. The tub of claim 5, wherein the insulating material comprises silicone and/or silicone foam.

7. The tub of claim 5, wherein the heating element is coated with the insulating material on a bottom side.

8. The tub of claim 1, wherein a hollow space is provided on one side of the heating element.

9. The tub of claim 8, wherein the hollow spaced is provided below the heating element.

10. The tub of claim 1, wherein the heating element comprises a plug or connector to electrically connect to the heating element.

11. The tub of claim 1, wherein the heating element comprises a tongue with electrical contacts.

12. The tub of claim 1, further comprising one or a combination of the following: temperature sensor, pressure sensor, humidity sensor, one or more LEDs, thermal overload protection, and/or means for sensing the level of the supply of liquid.

13. The tub of claim 1, wherein the lining forms a sealing lip at a top of the container.

14. The tub of claim 1, wherein the lining is thermally conductive to, in use, effectively transfer heat from the heating element to the supply of liquid.

15. A humidifier comprising a base station and a tub according to claim 1, wherein the tub is removably attached to the base station.

16. The humidifier of claim 15, wherein the base station comprises control electronics which are removably electrically connected to the heating element of the tub.

17. The tub of claim 1, wherein the tub further comprises a lid, and wherein the lining provides a sealing for the lid.

18. The tub of claim 1, wherein the lining is overmolded onto the inner surface of the side wall of the container.

19. Method of manufacturing a tub for a humidifier according to claim 1, comprising:
a) providing a tool for molding a container;
b) positioning a heating element inside said tool;
c) molding or injection-molding a container made of a first material around said heating element, wherein the container comprises a base and a side wall defining a reservoir for a supply of liquid to be evaporated, wherein the heating element is arranged only on an inner surface of the base of the container; and
d) molding a second material different from the first material over at least the heating element along the base of the container in order to provide a lining.

20. The method of claim 19, wherein a support structure is disposed between the heating element and the base of the container.

21. The method of claim 19, wherein the heating element is preheated to a predetermined temperature before the molding the first material.

22. The method of claim 21, wherein the predetermined temperature is between 50° C. and 200° C.

23. The method of claim 22, wherein the predetermined temperature is between 100° C. and 150° C.

* * * * *